United States Patent [19]

Enokizono et al.

[11] 4,252,899

[45] * Feb. 24, 1981

[54] PROCESS FOR IMMOBILIZING GLUCOSE ISOMERASE AND A METHOD OF CONTINUOUS ISOMERIZATION OF GLUCOSE

[75] Inventors: Shigehiro Enokizono, Ageo; Soichiro Ushiro, Kokubunji, both of Japan

[73] Assignee: CPC International Inc., Englewood Cliff, N.J.

[ * ] Notice: The portion of the term of this patent subsequent to Mar. 13, 1996, has been disclaimed.

[21] Appl. No.: 3,162

[22] Filed: Jan. 15, 1979

Related U.S. Application Data

[63] Continuation of Ser. No. 780,374, Mar. 23, 1977, Pat. No. 4,144,127.

[30] Foreign Application Priority Data

Apr. 2, 1976 [JP] Japan .................................. 51-36179

[51] Int. Cl.³ .............................................. C12P 19/24

[52] U.S. Cl. ...................................... 435/94; 435/176; 435/813

[58] Field of Search ........................... 435/94, 176, 813

[56] References Cited

U.S. PATENT DOCUMENTS

| | | | |
|---|---|---|---|
| 3,669,841 | 6/1972 | Miller | 435/176 |
| 3,796,634 | 3/1974 | Haynes et al. | 435/180 |
| 3,930,951 | 1/1976 | Messing | 435/176 |
| 3,933,587 | 1/1976 | Maeda et al. | 435/173 |
| 3,935,068 | 1/1976 | Nystrom | 435/94 |
| 3,956,065 | 5/1976 | Idaszak et al. | 435/94 |

*Primary Examiner*—Thomas G. Wiseman

[57] ABSTRACT

Glucose isomerase is immobilized in an active form by adsorbing the glucose isomerase onto a colloidal silica. The enzyme is contacted with the colloidal silica and the resulting composite solidified by freezing. Optionally, the composite may be gelatinized prior to freezing. The composite is then used for the isomerization of glucose to fructose.

3 Claims, No Drawings

PROCESS FOR IMMOBILIZING GLUCOSE ISOMERASE AND A METHOD OF CONTINUOUS ISOMERIZATION OF GLUCOSE

CROSS REFERENCE TO RELATED APPLICATION

This application is a continuation of application Ser. No. 780,374 filed Mar. 23, 1977, now U.S. Pat. No. 4,144,127.

This invention relates to a method for immobilizing glucose isomerase as well as to a method of isomerizing glucose continuously. One object is to obtain a immobilized glucose isomerase convenient for use in carrying on the continuous isomerization of glucose, or for industrial scale production. Another object is to develop a method of isomerizing glucose continuously and easily using the said immobilized glucose isomerase.

Since glucose isomerase was discovered as a product of microorganisms, the industrial production of glucose isomerase has been increasing abruptly especially in recent years. Glucose isomerase is the general name for the enzyme class which converts glucose (dextrose) into fructose (levulose). Glucose isomerase is mainly being used for the production of levulose-bearing syrup (LB syrup) from glucose on an industrial scale.

At present, industrial production of LB syrup is conducted by keeping glucose in contact with microbial cells containing glucose isomerase, at a temperature between about 60° C. and 70° C. for about 2-3 days. When using a batch system however, this conventional method has the disadvantage that the efficiency of utilization of the enzyme is low. Another disadvantage is that product purification costs are expensive, because it becomes colored during the reaction conducted at high temperatures for a long time. Furthermore, this method requires an expensive equipment; for example, a large tank for the reaction. In order to solve these problems of the conventional method, a lot of research is being done, which is mostly related to preparation of an immobilized glucose isomerase.

In recent years, various methods of immobilizing glucose isomerase have been developed. These methods, roughly speaking, can be divided into the following groups: (1) Glucose isomerase is combined with water-insoluble carriers or is adsorbed on a carrier. For instance, the method of having glucose isomerase adsorbed on an organic polymer consisting of poly-phenol (Japanese Pat. NS No. 49-80160), the method of having glucose isomerase adsorbed on porous alumina (Japanese Pat. NS No. 49-110889), the method of having glucose isomerase adsorbed on an anion exchange resin (U.S. Pat. No. 3,788,945), or the method of having glucose isomerase on DEAE-cellulose (U.S. Pat. No. 3,708,397). (2) Glucose isomerase is bridged with compounds having more than 2 functional groups. For instance, the method of glutaraldehyde treatment of microbial cells containing glucose isomerase (Japanese Pat. NS No. 48-1181; and the method of adsorption of glucose isomerase onto colloidal particles and subsequent treatment thereof with glutaraldehyde. (U.S. Pat. No. 3,796,634). (3) Glucose isomerase is confined in a gel lattice or in a semipermeable membrane. For instance, the method of fixing glucose isomerase by gelatinization through irradiation with ionized radioactivity of a mixture of glucose isomerase and acrylamide monomer (Japanese Pat. NS No. 49-81585). However DEAE-cellulose, under the method of group (1), is too expensive as a carrier to be used for conducting continuous isomerization of glucose on an industrial scale. On the other hand, immobilized glucose isomerase prepared by the methods of groups (2) and (3) shows bad flow properties when packed in a column. On the other hand, immobilized glucose isomerase prepared by the methods given in public disclosure of Japanese Pat. No. S48(1973)-1181 and (3) shows bad flow properties when packed in a column. Also, applying the method of U.S. Pat. No. 3,796,634 of (2) gives a carrier which is very difficult to pack in a column and if it could be packed, the flow properties may also be very bad. Therefore, it is difficult to maintain a constant flow therewith for a long time.

The inventors made every effort for the purpose of developing an immobilized glucose isomerase which gives good flow properties in a column and can be produced at a low cost. Coagulation, gelation and solidification of colloidal silica by freezing, freeze-drying, spray-drying, addition of salt and oxidation are well-known and can be found in, for example, Du Pont's Lucox catalogue. As a result, they found that the desired end can be attained by using colloidal silica as a carrier for the glucose isomerase. This invention is based on this finding.

The invention consists of:

(1) A process for immobilizing glucose isomerase comprising, adsorbing a glucose isomerase in a colloidal silica by contacting said enzyme with said colloidal silica, then solidifying the glucose isomerase adsorbed silica by freezing, as it is after gelatinization.

(2) A process for immobilizing glucose comprising, contacting continuously a glucose-containing solution with the immobilized glucose isomerase as defined in (1) to isomerize said solution.

The colloidal silica to be used in this invention covers all colloidal silica. For example, (1) the colloid of silica prepared by suspending super-fine particles of anhydrous silica in water, or (2) the colloid of which the $H^+$ of the OH ions on the surface of the particles was replaced by a cation such as $Na^+$, $K^+$, or $NH_4^+$. As its embodiment, for instance, there are LUDOX HS-30, LUDOX HS-40, LUDOX AM and LUDOX TM (all trademarks of and produced by Du Pont, USA), and SNOWTEX 20, SNOWTEX 30 and SNOWTEX N (all trademarks of and produced by Nissan Chemical Co., Japan). The colloidal silicas on the market have a particle size in the range of about 10–30 m$\mu$ in diameter. But colloidal silica can be used in this invention in any form, regardless of the particle size. Any available glucose isomerase enzyme preparation may be used in the process of this invention.

As examples of such glucose isomerases useful in this invention, microbial glucose isomerase is given which originates from the cells of ray fungi (such as *Streptomyces olivochromogenes*) or bacterial (such as *Lactobacillus brevis*) known as glucose isomerase producing microorganisms. This enzyme can be used in three different forms; namely, (1) crude glucose isomerase extracted from the cells of the glucose isomerase producing microorganisms either by autoylsis or by super-conic treatment, and separated from the cellular debris, (2) partially purified glucose isomerase treated with protamine to precipitate the nucleic acids, (3) crystalline glucose isomerase obtained by crystallization from partially purified glucose isomerase after fractionation with ammonium sulfate. One unit of enzyme activity is defined as the amount of enzyme which forms 1 mM fructose in one minute when incubated with a 0.1 M glucose solution in the presence of 0.01 M $MgCl_2$ and 0.001 M $CoCl_2$ (CPC unit).

The method of adsorbing glucose isomerase onto the colloidal silica is as follows. The glucose isomerase is used in solution form after proper dilution with water or a proper solution of salt (such as 0.001 M $MgCl_2$ of $MgSO_4$), preferably to about 10–30% by weight.

When glucose isomerase is adsorbed is adsorbed onto the colloidal silica, a proper amount of glucose isomerase is added to the colloidal silica, and the mixture is stirred for the proper period of time at the proper speed. For instance, glucose isomerase (as a dry base) at about $\frac{1}{3}$–1 weight ratio of the colloidal silica, and the mixture is stirred for about 10–20 minutes at 10–100 rpm. During stirring, the pH value of the mixture of the colloidal silica and enzyme is adjusted to the range of about 5–9 (preferably amount 6–8), either with a proper acid or alkali. For this, it is favorable, however, to use 1 N HCL or 1 N NaOH. More than 90% of the glucose isomerase used is adsorbed onto the surface of the particles of the colloidal silica by the method of this invention.

Furthermore, it is better to add a bifunctional reagent (such as glutaraldehyde) to the mixture of colloidal silica and glucose isomerase after the adorption reaction is finished. For instance, glutaraldehyde (as d.s.) is added to the mixture at about 1/10–1/5 the weight of the glucose isomerase (as d.s.) in the mixture, and this is followed by stirring for a proper period of time (about 30–60 minutes at room temperature. The adsorption ratio of glucose isomerase onto the colloidal silica becomes higher by this step, compared to when no bifunctional reagent is added. But is not an essential step to add a bifunctional reagent to the mixture.

Next, the glucose isomerase adsorbed colloidal silica is subjected to freezing in order to solidify it. The said colloidal silica can be subjected to freezing as such, or after suitable gelatinization.

To gelatinize the glucose isomerase adsorbed colloidal silica, a proper amount, for example between about 0.1 to 2 M (preferably about 0.1 to 0.3 M) concentration in the colloidal silica, of an appropriate salt, for example, $MgCl_2$, $MgSO_4$, NaCl or KCl (preferably $MgCl_2$) is added to it. This is stirred gently for a period of time, for example, about 10 to 30 minutes at room temperature. The glucose isomerase adsorbed colloidal silica, or the product gelatinized in accordance with the above method, is frozen in a freezing chamber at about $-10°$ to $-30°$ C. for a certain period of time, for example, about 20 to 40 hours, or by repetition of freezing and thawing for about 20 to 30 hours at proper intervals, for example, about every 5 hours, or by freezing for a certain period of time, for example, about 20 to 40 hours, while stirring.

The frozen product is readily thawed by just allowing it to stand at room temperature.

By this thawing process, a mixture consisting of solid silica with fixed glucose isomerase and a liquid fraction is obtained. The adsorbed glucose isomerase can easily be isolated from the mixture by a proper method, for example, filtration. The fixed glucose isomerase thus prepared is a semi-transparent granule or flake of 20 to 100 mesh and contains about 30 to 50% moisture. It is no longer soluble in water or a salt solution, but its enzymatic properties are almost the same as those of the untreated glucose isomerase. No remarkable decrease in enzymatic activity was found even after 6 months' refrigeration at 5° C.

The advantages of this invention's fixation method of glucose isomerase are: No decrease in enzyme activity during the fixation process, very strong binding of enzyme, its simple procedure, and low cost. Therefore, the invented method provides for very efficient glucose isomerase fixation.

Isomerization of glucose by using the immobilized isomerase thus prepared is as follows.

The glucose-sontaining solution used in the invented process may consist of either starch saccharizate of about DE 90–99 (DE: Dextrose quivalent percentage of reducing sugars indicated as dextrose against the total amount of solid, refined starch saccharizate which is prepared by refining, for example, on an ion exchange resin, a dextrose solution prepared by dissolving a total sugar or crystalline dextrose, or a hydrol which is produced during dextrose production. These glucose-containing solutions are either concentrated or diluted in order to adjust them to about 20–60% (d.s.), preferably around 50%. The pH is also adjusted to about 7 to 9, preferably about 7.5 to 8.5, with an alkali, for example, NaOH or KOH. Prior to isomerization, about 1 to 10 mM of a proper glucose isomerase activator, preferably $MgCl_2$, may be added. Also, a chelating agent, for example EDTA, can be added to the solution to remove isomerization inhibitors such as $Zn^{++}$, etc.

The fixed glucose isomerase prepared through the previously mentioned process either with or without sieving is poured into a column. Then the column is filled either with water, a diluted salt solution, for example, $MgCl_2$ solution, or a glucose-containing solution and kept at a proper temperature, preferably about 60° to 70° C. Continuous isomerization is carried out by passing through the column a glucose-containing solution prepared according to the above method. The flow rate should be SV about 1 to 10 (SV: Space Velocity, indicates the hourly amount of solution passed through the column in terms of the proportion to the bed-volume of the column), preferably, about 2 to 5. Either ascending or descending flow is possible.

Since the glucose isomerase is fixed on granules, the glucose-containing solution can flow smoothly through the column, hence, the flow rate can be readily adjusted to achieve any given isomerization rate. Because of the continuous isomerization, the reaction period is very short. Consequently, the pH of the solution and the reaction temperature can be readily adjusted to the optimum for glucose isomerase.

To adjust the pH of the glucose-sontaining solution to around 7.5 to 8.5 is desirable for enhancing enzyme stability during the isomerization using the fixed isomerase.

The amount of glucose isomerase required is about 0.2 to 0.4 units for isomerization of 1 g of glucose (as dry basis) into 45% isomerized sugar by the continuous process until the half-life of the enzyme activity is reached (see below). The conventional batch process requires about 2 units of glucose isomerase to achieve the same degree of isomerization. Using this invention's continuous isomerization method, the half-life of the enzyme activity means the length of time (days) from the start to the point where the fructose content of the effluent becomes half of that in the initial effluent.

As stated above, this continuous isomerization method requires only 1/5 to 1/10 of the glucose isomerase needed by the batch process to achieve the same degree of isomerization. Because of the rapid isomerization reaction and since there is practically no salt formation during isomerization, the product of this process has little color and refining of the product can also be very simplified. Namely, only desalting on an ion exchange resin is required for the product of this process, while products of the conventional batch process may require refining through several IER columns and also decolorization with active carbon. Besides, the batch process requires a large reaction tank and complicated refining equipment, while this process requires only several columns.

As mentioned above, big savings of isomerase and investment for facilities are expected with this process, hence manufacturing costs can be remarkably reduced.

The process of this invention is further illustrated in the following examples. The examples are not intended to limit the scope of this invention in any manner.

EXAMPLE I

One hundred milliliters of commercial colloidal silica, LUDOX HS-30 (produced by Du Pont Co., USA) was introduced into a beaker (300 ml volume) and was diluted with 160 ml of deionized water. The pH of this solution was then adjusted to 7.0 with 1 N HCl. After that, 35 ml of enzyme solution containing 41,500 units of glucose isomerase was added to said solution. The enzyme solution had been prepared form the cells of *Streptomyces olivochromogenes*, liquid cultured for 50 hours, through digestion with lysozyme and partial purification using isopropyl alcohol. Next, the mixture was gently agitated at room temperature for 15 minutes. Next 2 ml of 25% commercial glutaraldehyde solution (produced by Tokyo Kasei Kogyo Co.) was added to the resulting solution. The solution was then gently agitated at room temperature for 60 minutes. Next, 15 g of $MgCl_2.6H_2O$ was added to the solution. The solution was then gently agitated at room temperature for 30 minutes. Then, the mixture was placed in a freezer kept at a temperature of $-20°$ C. After 12 hours, the frozen mixture was taken out of the freezer and was stirred at room temperature. The mixture was separated in the beaker into two portions, a solid phase and a liquid phase. The mixture was then placed again in the freezer for 12 hours. Then, the mixture was stirred again at room temperature and was separated again into two portions, the solid phase and the liquid phase. The liquid phase was removed from the mixture by decantation. Fifty grams of solid material was obtained. The solid material, which contains immobilized glucose isomerase, had 790 units of glucose isomerase activity per gram of solid material (as is).

EXAMPLE II

One hundred milliliters of commercial colloidal silica, LUDOX HS-30 (produced by Du Pont Co., USA) was introduced into a beaker (300 ml volume) and was diluted with 160 ml of deionized water. The pH of this solution was then adjusted to 7.0 with 1 N HCl. After that, 35 ml of enzyme solution containing 41,500 units of glucose isomerase was added to the said solution. The enzyme solution had been prepared by the method described in Example I. Next, the mixture was gently agitated at room temperature for 30 minutes. Next 15 g of $MgCl_2.6H_2O$ was added to the resulting solution. The solution was then gently agitated at room temperature fro 30 minutes. Then the mixture was placed in a freezer kept at room temperature of $-20°$ C. After 12 hours, the frozen mixture was taken out of the freezer, and was stirred at room temperature. The mixture was separated in the beaker into two portions, a solid phase and a liquid phase. The mixture was then placed again in the freezer for 12 hours. Then, the mixture was stirred again at room temperature and was separated again into two portions, the solid phase and the liquid phase. The liquid phase was removed from the mixture by decantation. Thirty-eight grams of solid material was obtained. The solid material, which contains immobilized glucose isomerase, had 550 units of glucose isomerase activity per gram of solid material (as is).

EXAMPLE III

One hundred milliliters of commercial colloidal silica, LUDOX HS-30 (produced by Du Pont Co., USA) was introduced into a beaker (200 ml volume) and was diluted with 160 ml of deionized water. The pH of this solution was then adjusted to 7.0 with 1 N HCl. After that, 35 ml of enzyme solution containing 41,500 units of glucose isomerase was added to the said solution. The enzyme solution had been prepared by the method described in Example I. Next, the mixture was gently agitated at room temperature for 15 minutes. Next, 2 ml of 25% commercial glutaraldehyde solution (product by Tokyo Kasei Kogyo Co.) was added to the resulting solution. The solution was then gently agitated at room temperature for 60 minutes. Then the mixture was placed in a freezer kept at room temperature of $-20°$ C. After 12 hours, the frozen mixture was taken out of the freezer and was stirred at room temperature. The mixture was separated in the beaker into two portions, a solid phase and a liquid phase. The mixture was then placed again in the freezer for 12 hours. Then, the mixture was stirred again at room temperature, and was separated again into two portions, the solid phase and the liquid phase. The liquid phase was removed from the mixture by decantation. Forty grams of the solid material was obtained. The solid material which contains immobilized glucose isomerase, has 420 units of glucose isomerase activity per gram of solid material (as is).

EXAMPLE IV

One hundred milliliters of commercial colloidal silica, LUDOX AM (produced by Du Pont Co., USA) was introduced into a beaker (300 ml volume) and was diluted with 160 ml of deionized water. The pH of this solution was then adjusted to 7.0 with 1 N JCl. After that, 35 ml of enzyme solution containing 41,500 units of glucose isomerase was added to said solution. The enzyme solution has been prepared by the method described in Example 1. Next, the mixture was gently agitated at room temperature for 15 minutes. Next 2 ml of 25% commercial glutaraldehyde solution (produced by Tokyo Kasei Kogyo Co.) was added to the resulting solution. The solution was then gently agitated at room temperature for 60 minutes. Next, 15 g of $MgCl_2.6H_2O$ was added to the solution. The solution was then gently agitated at room temperature for 30 minutes. Then, the mixture was placed in a freezer kept at a temperature of $-20°$ C. After 12 hours the frozen mixture was taken out of the freezer and was stirred at room temperature. The mixture was separated in the beaker into two portions, a solid phase and a liquid phase. The mixture was then placed again in the freezer for 12 hours. Then, the mixture was stirred again at room temperature and was separated again into two portions, the solid phase and the liquid phase. The liquid phase was removed from the mixture by decantation. Thirty-five grams of solid material was obtained. The solid material, which contains immobilized glucose isomerase, had 423 units of glucose isomerase activity per gram of solid material (as is).

EXAMPLE V

One hundred milliliters of commercial colloidal silica, SNOWTEX-30 (produced by Nissan Kagaku Co.) was introduced into a beaker (300 ml volume) and was diluted with 160 ml of deionized water. The pH of this solution was then adjusted to 7.0 with 1 N HCl. After that, 35 ml of enzyme solution containing 41,500 units of glucose isomerase was added to said solution. The enzyme solution had been prepared by the method described in Example I. Next, the mixture was gently agitated at room temperature for 15 minutes. Next, 2 ml of 25% commercial glutaraldehyde solution (produced by Tokyo Kasei Kogyo Co.) was added to the resulting solution. The solution was then gently agitated at room temperature for 60 minutes. Next, 15 g of $MgCl_2.6H_2O$ was added to the solution. The solution was then gently agitated at room temperature for 30 minutes. Then, the mixture was placed in a freezer kept at a temperature of $-20°$ C. After 12 hours the frozen mixture was taken out of the freezer and was stirred at room temperature. The mixture was separated in the beaker into two portions, a solid phase and a liquid phase. The mixture was the placed again in the freezer for 12 hours. Then, the mixture was stirred again at room temperature and was separated again into two portions, the solid phase and the liquid phase. The liquid phase was removed from the mixture by decantation. Thirty-six grams of solid material was obtained. The solid material, which contains immobilized glucose isomerase, had 455 units of glucose isomerase activity per gram of solid material (as is).

EXAMPLE VI

Fifty grams of the immobilized glucose isomerase (moist) (Bed volume: 60 ml), prepared by having glucose isomerase adsorbed onto LUDOX HS-30 according to the procedure described in Example I, was packed in a jacketed glass column (2.5×20 cm). With the column held at a temperature of 60° C., a 50% glucose solution containing 5 mM $MgCl_2$ and adjusted to a pH of 8.0 was passed through it at a constant flow rate of SV 2. The fructose content of the effluent was 51.2% of the solid substrate at first. This value was held for 10 days and then decreased slowly to 25.6%, half of the initial value, after 75 days.

EXAMPLE VII

Thirty-eight grams of the immobilized glucose isomerase (moist) (Bed volume: 45 ml) prepared by having glucose isomerase adsorbed onto LUDOX HS-30 according to the procedure described in Example II was packed in a jacketed glass column (2.5×20 cm). With the column held at a temperature of 60° C., a 50% glucose solution containing 5 mM $MgCl_2$ and asjusted to pH 8.0 was passed through it at a constant flow rate of SV 2. The fructose content of the effluent was 51.2% of the solid substrate at first. This value was held for 5 days and then decreased to 25.6%, half of the initial value, after 38 days.

EXAMPLE VIII

Forty grams of the immobilized glucose isomerase (moist) (Bed Volume: 48 ml) prepared by having a glucose isomerase adsorbed onto LUDOX HS-30 according to the procedure described in Example III was packed in a jacketed glass column (2.5×20 cm). With the column held at a temperature of 60° C., a 50% glucose solution containing 5 mM $MgCl_2$ and adjusted to pH 8.0 was passed through it at a constant flow rate of SV 2. The fructose content of the effluent was 51.2% of the solid substrate at first. This value was held for 2 days and then decreased to 25.6%, half of the initial value, after 30 days.

EXAMPLE IX

Thirty-five grams of the immobilized glucose isomerase (moist) (Bed volume: 40 ml) prepared by having glucose isomerase adsorbed onto LUDOX AM according to the procedure described in Example IV was packed in a jacketed glass column (2.5×20 cm). With the column held at a temperature of 60° C., a 50% glucose solution containing 5 mM $MgCl_2$ and adjusted to pH 8.0 was passed through it at a constant flow rate of SV 2. The fructose content of the effluent was 51.2% of the solid substrate at first. This value was held for 1 day and then decreased to 25.6%, half of the initial value, after 15 days.

EXAMPLE X

Thirty-six grams of the immobilized glucose isomerase (moist) (Bed volume: 42 ml) prepared by having glucose isomerase adsorbed onto SNOWTEX 30 according to the procedure described in Example V was packed in a jacketed glass column (2.5×20 cm). With the column held at a temperature of 60° C., a 50% glucose solution containing 5 mM $MgCl_2$ and adjusted to pH 8.0 was passed through it at a constant flow rate of SV 2. The fructose content of the effluent was 51.2% of the solid substrate at first. This value was held for 4 days and then decreased to 25.6%, half of the initial value, after 30 days.

EXAMPLE XI

Fifty grams of the immobilized glucose isomerase (moist) (Bed volume: 60 ml) prepared according to the procedure described in Example 1 was packed in a jacketed glass column (2.5×20 cm). With the column held at a temperature of 60° C., a 50% glucose solution containing 5 mM $MgCl_2$ and adjusted to pH 8.0 was passed through it at a variable flow rate to maintain a continuous isomerization rate (isomerization of 45% dextrose into fructose). To attain this isomerization rate, the initial flow rate was SV 6. The table shows the changes of the flow rate to maintain the constant isomerization rate.

| Days | 2 | 5 | 10 | 20 | 30 | 40 |
|---|---|---|---|---|---|---|
|  | 5.7 | 5.0 | 4.3 | 3.0 | 2.1 | 1.5 |

Throughout this continuous isomerization, the column showed very good flow properties.

While this invention has been described in connection with specific embodiments thereof, it will be understood that it is capable of further modification, and this application is intended to cover any varisations, uses or adaptations of the invention following, in general, the principles of the invention and including such departures from the present disclosure as come within the known or customary practice in the art to which the invention pertains and as may be applied to the essential features hereinbefore set forth, and as fall within the scope of the invention.

We claim:

1. A continuous process for isomerizing glucose comprising contacting a glucose-containing solution having a pH of about 7 to about 9 with an immobilized enzyme composite comprising immobilized, active glucose isomerase on solid granules or flakes of colloidal silica having a particle size of 20 to 100 mesh and containing about 30 to 50 percent moisture, said immobilized enzyme composite being produced by adsorbing glucose isomerase enzyme onto colloidal silica by contacting enzyme with said colloidal silica in aqueous medium, solidifying the glucose isomerase adsorbed silica by freezing and then thawing the resultant frozen composition.

2. The process of claim 1 wherein the glucose isomerase adsorbed silica is treated with bifunctional reagent prior to freezing.

3. The process of claim 2 wherein said composite is comprised of colloidal silica of about 10 to about 30 m$\mu$ in diameter.

* * * * *